(12) United States Patent
Mishima et al.

(10) Patent No.: US 6,391,263 B1
(45) Date of Patent: May 21, 2002

(54) AUTOMATED ANALYZING SYSTEM AND METHOD THEREFOR

(75) Inventors: Yoshihiro Mishima, Kobe; Noriyuki Narisada, Akashi, both of (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 09/512,709

(22) Filed: Feb. 25, 2000

(30) Foreign Application Priority Data

Feb. 26, 1999 (JP) .......................................... 11-051803

(51) Int. Cl.[7] .............................................. G01N 21/01

(52) U.S. Cl. ............................. 422/67; 422/73; 422/81; 436/43; 436/47; 700/266

(58) Field of Search ............................. 422/67, 73, 81; 436/43, 47; 700/266, 226

(56) References Cited

U.S. PATENT DOCUMENTS

| | | | | |
|---|---|---|---|---|
| 5,187,673 A | * | 2/1993 | Carvert, Jr. et al. | |
| 5,380,491 A | * | 1/1995 | Carver, Jr. et al. | |
| 5,656,499 A | * | 8/1997 | Chupp et al. | |
| 5,728,351 A | * | 3/1998 | Calvert, Jr. | |

* cited by examiner

*Primary Examiner*—Ana Fortuna
(74) *Attorney, Agent, or Firm*—Shinjyu Global IP Counselors, LLP

(57) ABSTRACT

To facilitate operations wherein samples from different animal types are assayed in succession, disclosed is the provision of an animal type table wherein correspondences between animal type and identifying information designating the animal type are assigned and stored; an animal type input means for inputting, utilizing the identifying information, animal type of a vital sample to be analyzed; and analysis configuration means for altering analysis condition settings in accordance with inputted animal type. The animal type table settings are best user-configurable to suit the user's running of the automated analyzing system.

22 Claims, 9 Drawing Sheets

| ID | Animal Type |
|---|---|
| 1 | Rat |
| 2 | Monkey |
| 3 | Dog |
| ⋮ | ⋮ |

AUTOMATED ANALYZING SYSTEM AND METHOD THEREFOR

BACKGROUND OF THE INVENTION

1. Technical Field

The present invention relates to analyzing systems that analyze blood, urine and like vital samples. The invention relates more particularly to an analyzing system that analyzes vital samples from a plurality of animal type under analysis conditions adapted to the animal type.

2. Description of Related Art

Various tests such as blood tests, biochemical examination, and general screenings are conducted as clinical trials utilizing human blood, urine and like vital samples. Such trials have application not only to human beings, but also to dogs, rats, and other animals, and are conducted likewise.

Nevertheless, because the components of vital samples, for example erythrocyte cell size and density, differ from human beings according to the type of animal, there will be instances in which analyzing systems for humans cannot be employed as is. In these cases, the analysis is performed matching analyzing system analysis conditions to the animal type of the sample to be measured, by varying, for example, analyzing program and measurement sensitivity, and furthermore, reaction time and assaying reagents.

To assay mingled samples wherein the analysis conditions differ among them, with a single analyzing device the analysis conditions have to be re-set corresponding to the animal type with every measurement, or separate analyzing devices have to be readied for each of the species.

An analyzing device having a broad measuring range must be employed wherein samples of differing species are to be assayed with the same analyzing device, so as to be able to assay any of the animal types among them. Employing such an analyzing device presents technical difficulties depending on the animal type and the assay items, which otherwise raise the cost of the analyzing device itself.

Further, even being able to keep the target assays for different animal type within the assaying range of a single analyzing device, there will be instances in which reliable results cannot be obtained by performing merely the same analysis on the quantitative results for the different animal type. For example, wherein a plurality of cell types are analyzed in a two-dimensional scattergram based on a plurality of detection signals, there will be cases in which the characteristics of each detection signal for each cell will differ according to the animal type. Reliable data cannot be obtained unless the detection signal analytical method accommodates these characteristics. Accordingly, getting the assay method to be common to all of the animal type is difficult.

Further still, assaying different animal type with a single analyzing device has the following problems. FIG. 10 depicts an animal type input screen in a conventional analyzing device. A window 71 is provided on the input, screen for inputting animal type. When a user clicks on the arrow in the window 71, a list of configurable animal type is displayed, enabling the animal type that is to be assayed to be set. This operation is done each and every time an assay is made. Herein, changing animal type wherein vital samples of different animal type are mingled is a very involved operation. Further, wherein analyzing devices are prepared for each animal type, just that animal type number of analyzing devices becomes the plurality needed, elevating costs.

SUMMARY OF THE INVENTION

An object of the present invention is to provide an analyzing device enabling analysis with ease of operation wherein differing samples of animal type are mingled.

The foregoing circumstances have been taken into consideration in the present invention. Therefore, the invention of the present application in a first aspect provides an automated analyzing system that analyzes vital samples from different animal types, the automated analyzing system characterized in being provided with an animal type table, an animal type input means, and an analysis configuration means.

The animal type table assigns correspondences between and stores animal type and identifying information designating the animal type. The animal type input means functions to input, utilizing the identifying information, animal type of a vital sample that is analyzed. With the analysis configuration means, analysis condition settings are altered in accordance with inputted animal type.

Various modes for inputting the identifying information herein might be given as examples: manual input by a user, automated input by reading from a barcode or IC chip, or automated input by instructions from a host computer. The identifying information consists of, for example, one or two alphanumeric characters.

The invention of the present application in a second aspect provides, in the automated analyzing system of the foregoing first aspect of the invention, the analysis configuration means altering measurement sensitivity in conformance with the inputted animal type.

For example, in analyzing blood, erythrocyte size will vary greatly depending on the animal type. Herein, the measurement sensitivity is altered in correspondence with the animal type.

The invention of the present application in a third aspect provides, in the automated analyzing system of the foregoing first aspect of the invention, the analysis configuration means assaying measurement data utilizing an assaying program adapted to the inputted animal type.

For example, in analyzing leukocytes, parameters and reference values for assaying the five classes of leukocytes differ with each animal type. Herein, the automated analyzing system analyzes measurement data utilizing parameters and reference values adapted to the inputted animal type.

In a fourth aspect the invention of the present application provides, in the automated analyzing system of the foregoing third aspect of the invention, the assaying program demarcation analyzing a two-or-more-dimensional scattergram based on measurement data for two or more species.

For example, from measurement data by flow cytometry, the assaying program expresses size and interior structural information of an analytical object in a two-dimensional graph, and designates the analytical object on the graph from cluster size and position.

In a fifth aspect the invention of the present application provides, in the foregoing first aspect of the invention, the automated analyzing system further equipped with configuration means for receiving a setting that assigns correspondences between animal types in the animal type table and the identifying information that designates animal types.

This system has the advantage that the user can, with the user's own running of the automated analyzing system, configure the assignment of correspondences between animal type and identifying information.

The invention of the present application in a sixth aspect provides and automated analyzing method utilized in an automated analyzing system for analyzing vital samples from different animal type, the automated analyzing method:

(A) preparing an animal type table wherein correspondences between animal type and identifying information designating said animal type are assigned and stored;

(B) inputting, utilizing said identifying information, animal type of a vital sample to be analyzed; and (C) altering analysis condition settings in accordance with inputted animal type.

The effective results are similar to the invention in foregoing first aspect.

In a seventh aspect the invention of the present application provides a computer-readable recording medium wherein a program for executing the foregoing automated analyzing method is recorded. Examples that might be given of recording media herein are computer-readable floppy disks, hard disks, semiconductor memory, CD-ROMs, DVDs, and magneto optical disks (MOs).

In an eighth aspect the invention of the present application provides a transmission medium transmitting a program for executing the foregoing automated analyzing method. Examples that might be given of transmission media herein are communications media (optical fibers, radio circuitry) in computer network (LAN, Internet, and radio communications network) systems for supplying program information by propagation as carrier waves.

The foregoing and other objects, features, aspects and advantages of the present invention will become more apparent from the following detailed description in conjunction with the accompanying drawings.

BRIEF DESCRIPTION OF THE DRAWINGS

FIG. 6 is a conceptual explanatory diagram of an animal type table;

FIG. 7 is an example of a configuration screen for the animal type table;

Figure 10:
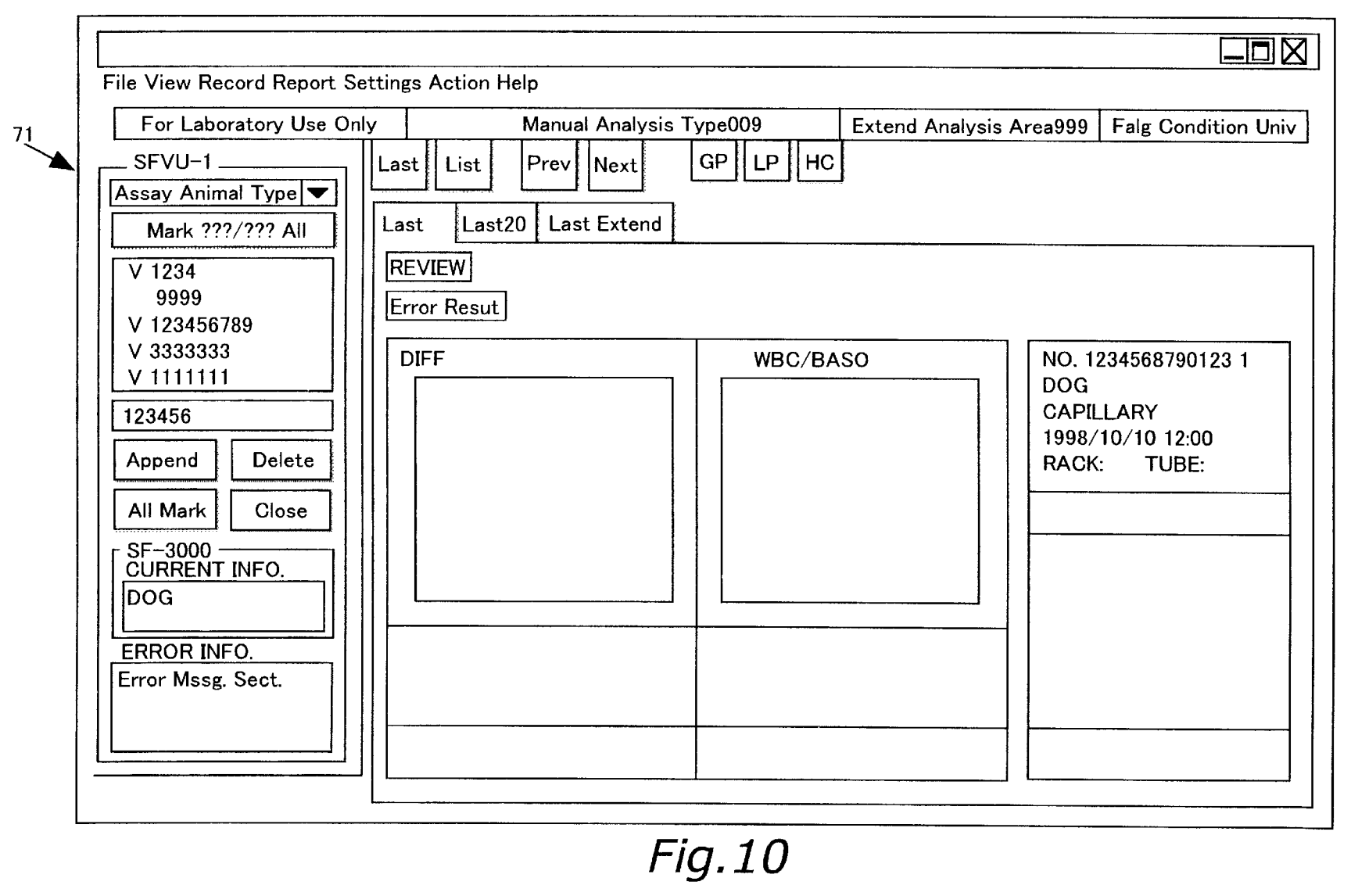

FIG. 10 is an explanatory diagram illustrating a conventional animal type input method.

DETAILED DESCRIPTION OF THE PREFERRED EMBODIMENTS

Examples that can be given of analyzing systems to which the present invention is applicable are blood analyzing systems and biochemical assaying systems. Animal types that are assayed would include dogs, cats, rats, and mice, as well as humans.

In the animal type table, correspondences are assigned between animal type and identifying information designating the animal type. An ID number made up of one or two alphanumeric characters, for example, can be used as identifying information. The animal type table, wherein there is a host computer, may be held in the host computer, or may be held in the controllers that constitute the automated analyzing System. A "host computer" is an information terminal that manages a plurality of analyzers and controllers and is connected to them via a network.

Examples that might be given of animal type input means are keyboards for manually inputting animal type IDs for assay samples, reception means for receiving ID signals from a host computer, and reading means for ID automated reading. "Automated reading" can be understood to be the reading of IDs from, for example, IC chips or barcodes on sample containers.

The following explains one embodiment of the present invention with reference to the drawings.

Figure 1A:
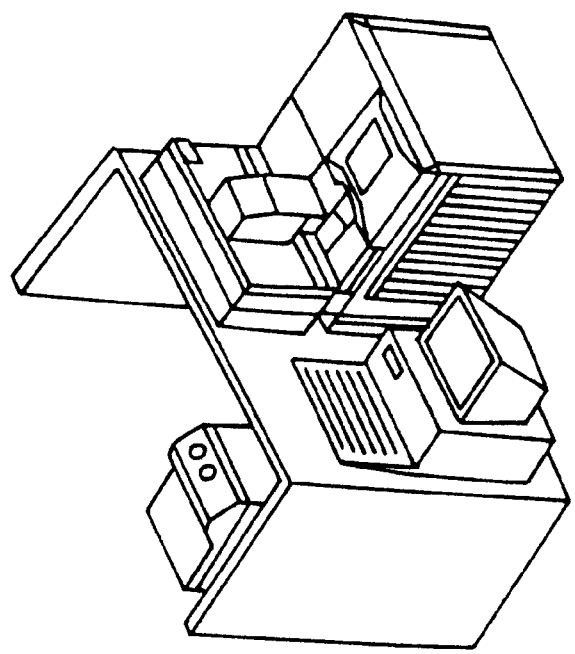
FIG. 1(a) and (b) are oblique views of an automated analyzing system for illustrating one embodiment of the present invention.
Figure 1B:
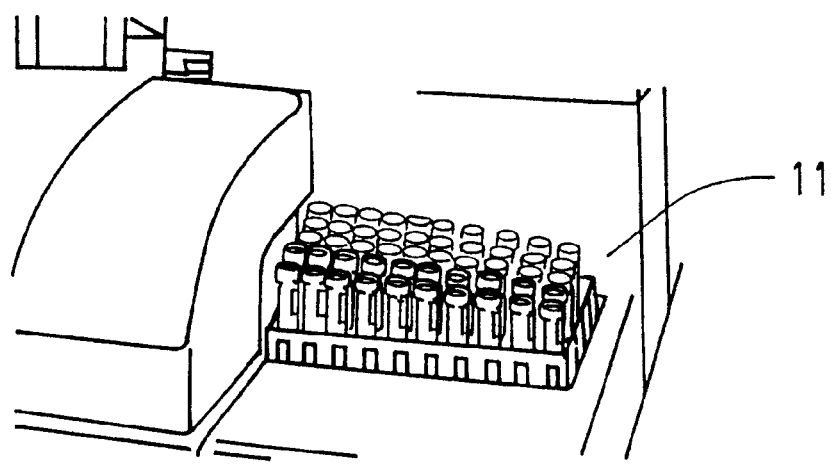

Explanation will be made wherein multi-item automated blood analyzing system SF-3000 (Sysmex Corp. mfr.) is employed as an automated analyzing system. FIG. 1(a) is an oblique view of an automated analyzing system in connection with the present embodiment. FIG. 1(b) depicts a section wherein samples are set in the analyzing system of FIG. 1(a).

Figure 2:
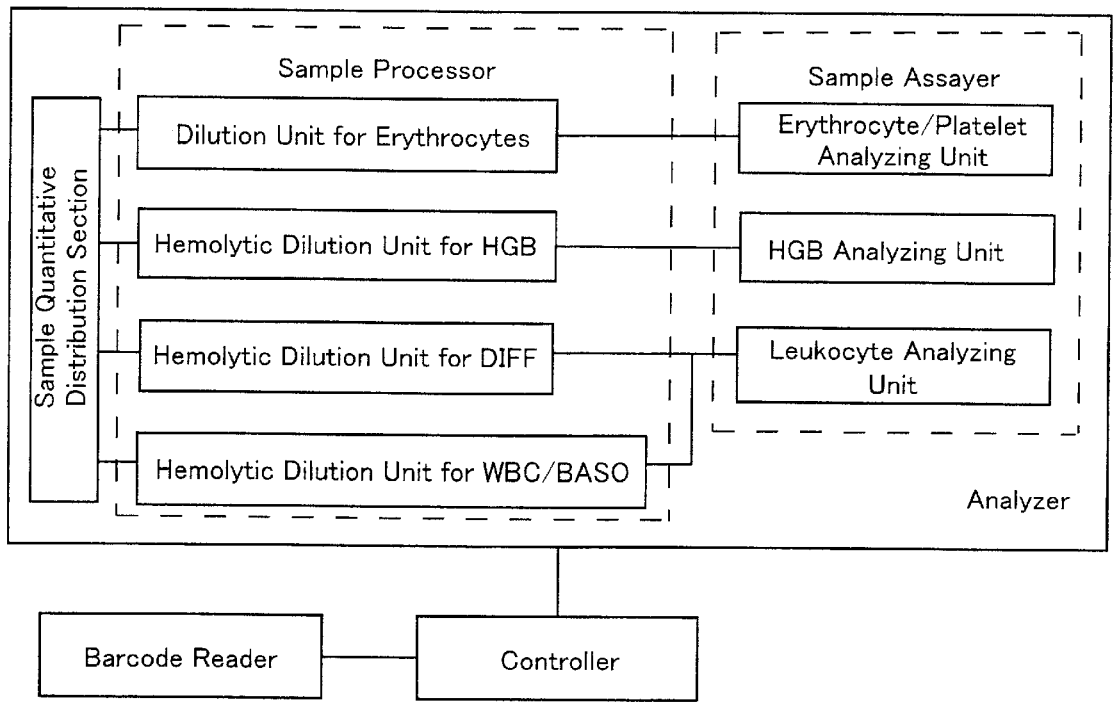
FIG. 2 is a configurational explanatory diagram of an automated analyzing system for illustrating one embodiment of the present invention.

FIG.2 is a bock diagram illustrating functions of the automated analyzing system. The automated analyzing system is made up of an analyzer and a controller that controls it. The analyzer has a sample quantitative distribution section, a sample processor, and a sample assayer. The sample assayer is provided with erythrocyte and platelet analyzing units, a leukocyte analyzing unit, and a hemoglobin (HGB) analyzing unit. To process the samples so that they are suitable for measurement by the sample assayer, the sample processor has: a dilution process unit for erythrocytes, a hemolytic dilution process unit for HGB, a hemolytic dilution process unit for differential (DIFF), and a hemolytic dilution process unit for white blood cells/basophils (WBC/BASO).

Analyzing operation by the automated analyzing system will be explained. Referring again to FIGS. 1(a) and (b), which depict overviews of the present analyzing system, blood to be analyzed is collected into vacuum sampling tubes that are stored thus in a rack 11, and set into the sampler of the analyzing system. In a sample aspirating section (not shown), a barcode reader reads barcodes pasted to the sampling tubes, and the sample tube IDs are recorded in the analyzing system. A sample-aspirating piercer then pierces the sample tubes, and the blood within the sample tubes is aspirated. A sampling valve in the sample quantitative distribution section quantitatively distributes the aspirated blood into four respectively determined sample volumes.

Figure 3:
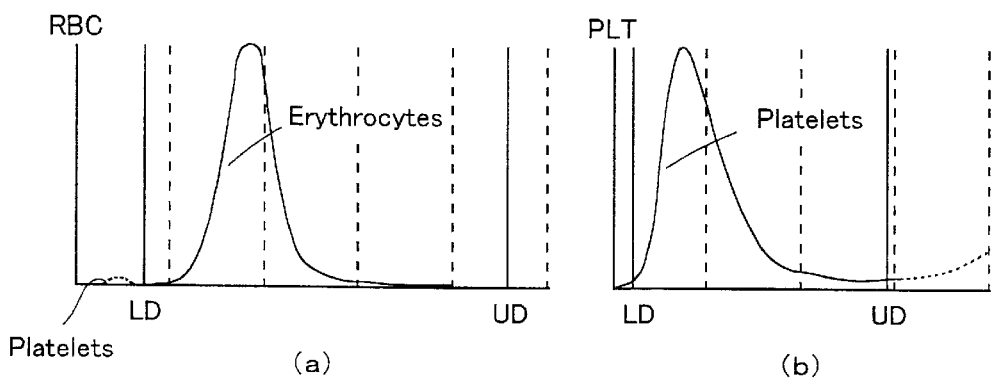
FIG. 3 is a particle-size distribution graph from an instance of assaying erythrocytes and platelets.

A first blood sample is sent to the dilution process unit for erythrocytes and is diluted with a diluent. It is then sent to the erythrocyte and platelet analyzing unit wherein the erythrocytes and platelets are measured by electrical signal changes when the blood cells are passed through a detection unit. In the present embodiment example, blood cell analysis is conducted by a DC (direct current) detection system. In a DC detection system, change in impedance across electric poles when cells pass through detection unit pores in which DC current is flowed expresses as pulses. Pulse height reflects the size of the detected cells. FIG. 3(a) and (b) show one example of results in which erythrocytes and platelets have been assayed by discriminating according to cell size. FIG. 3(b) is a magnified diagram of the assay results in FIG. 3(a) for platelets.

A second blood sample is sent to the hemolytic dilution process unit for HGB (hemoglobin) and hemolytically diluted with a diluent and a hemolyzing agent for HGB assay. It is then sent to the hemoglobin analyzing unit wherein HGB density is computed by measuring photo-absorbance.

A third blood sample is sent to the hemolytic dilution process unit for DIFF, wherein hemolytic dilution is carried out for approximately 10 seconds with a hemolyzing agent for the leukocyte classes. As a result, the erythrocytes are hemolyzed, the morphology of the leukocytes is retained, and the eosinophils of the leukocyte subpopulation are stained. The process liquid is sent to the leukocyte analyzing unit. The leukocyte analyzing unit conducts assays by flow cytometry.

Figure 4:
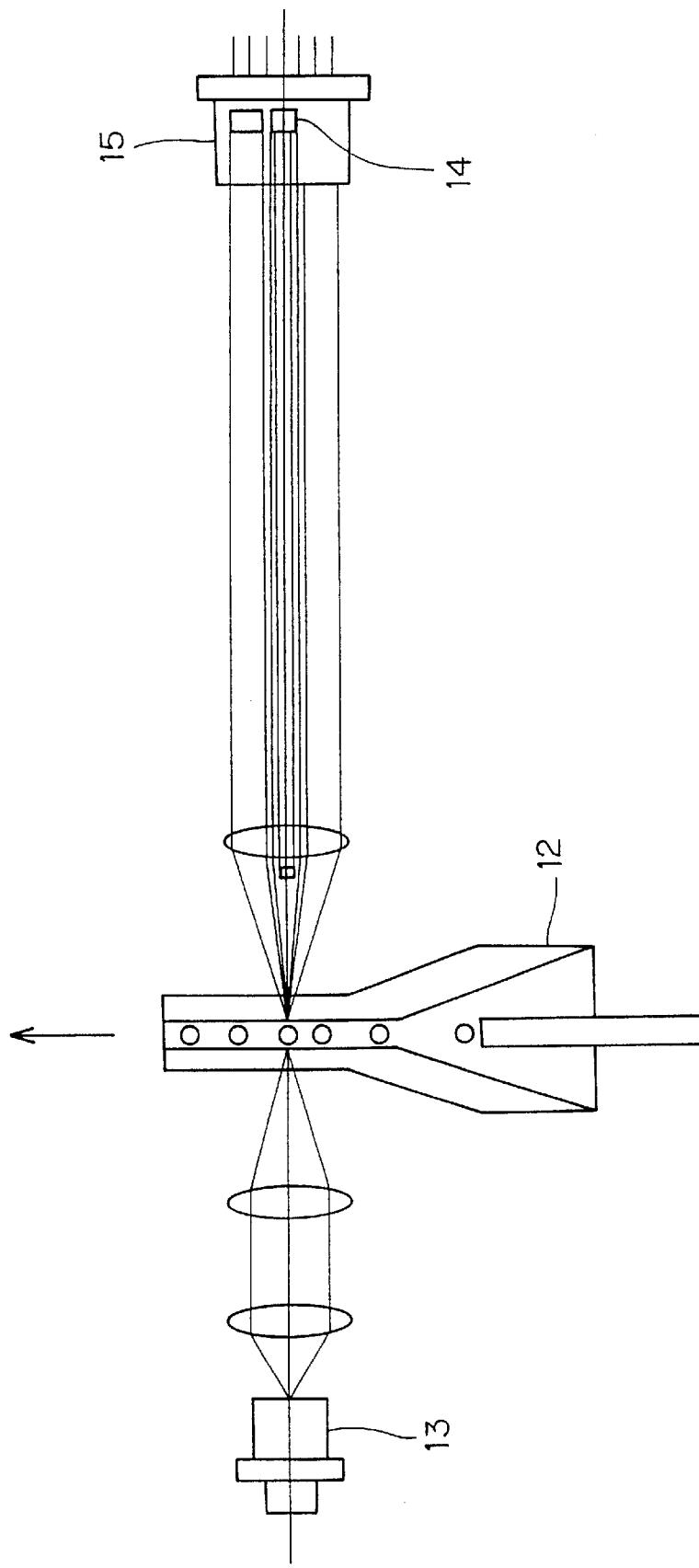
FIG. 4 diagrams flow-cytometry principles employed in a leukocyte analyzer.

FIG. 4 illustrates principles of assaying by flow cytometry. As shown in the figure, leukocytes are flowed one-by-one in a flow cell 12. The leukocytes are irradiated by a laser beam from a semiconductor laser 13, which yields low-angle forward-scattered light and high-angle forward-scattered light that is detected by respective photodiodes 14 and 15. The low-angle forward-scattered light reflects leukocyte size; the high-angle forward-scattered light reflects leukocyte inner morphology, such as nuclei and granules.

Figure 5:
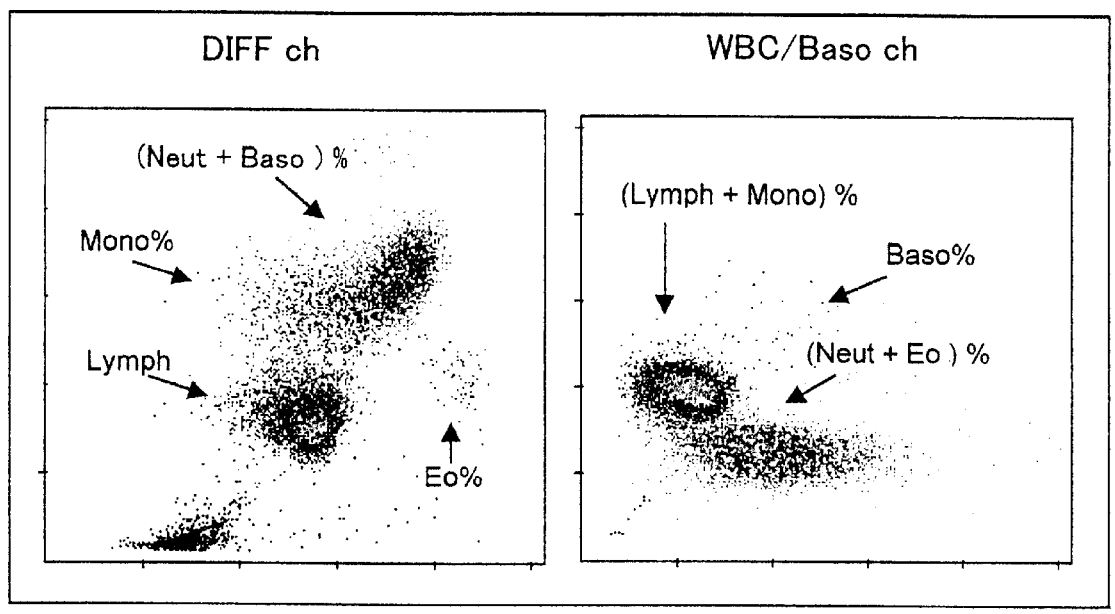
FIG. 5 is a scattergram showing an example of assay results for human leukocytes

FIG. 5 depicts an example of a scattergram yielded as a result of this assay. In the "DIFF ch" of FIG. 5, lymphocyte (Lymph), monocyte (Mono) eosinophil (Eo), and neutrophil and basophil (Neu+Baso) subpopulations have been demarcation-analyzed according to differences in leukocyte size and in the leukocyte internal information. The vertical axis is the high-angle forward-scattered light intensity, and the transverse axis the low-angle forward-scattered light intensity.

A fourth blood sample is sent to the hemolytic dilution unit for WBC/BASO, wherein a hemolytic dilution process is conducted for approximately 30 seconds with a hemolyzing agent for basohpils. As a result, the erythrocytes are hemolyzed, and the membranes of leukocytes apart from basophils are dissolved to become nuclei-naked and contracted. The process fluid is sent to the leukocyte analyzing unit, where by flow cytometry likewise as described earlier low-angle forward-scattered light and high-angle forward-scattered light are measured.

Reference is again made to the FIG. 5 depiction of a scattergram example yielded as a result of the sample assay. In the WBC/BASOch of FIG. 5, subpopulations of basophils (Baso), lymphocytes and monocytes (Lympho+Mono) and multinucleated cells apart from basophils (Neut+Eo) are demarcation-analyzed. The vertical axis is high-angle scatterd light intensity; the transverse axis, low-angle scatterd light.

Leukocyte counts, and particle counts and percentages for the five classes of leukocytes are computed according to the assay results for the third blood sample and the assay results for the fourth blood sample.

Figure 6:
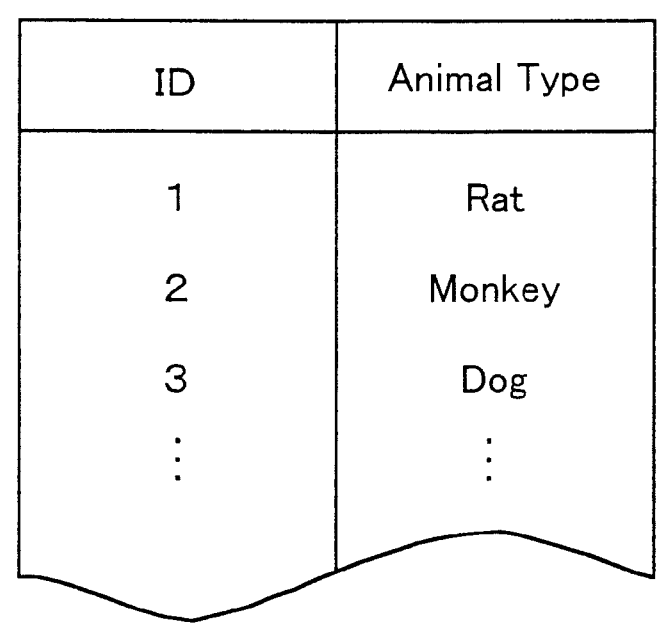

The automated analyzing system maintains an animal type table in which correspondences between analyzable animal types and IDs for designating the animal types are assigned. A conceptual explanatory diagram of an animal type table is shown in FIG. 6. The animal type table in the present embodiment example is held in the controller. Wherein the automated analyzing system has a plurality of analyzers and controllers that are managed with a host computer, the animal type table may be held in the host computer. Wherein the animal type table is held in the host computer, the controllers refer to the host computer for the animal types that correspond to inputted IDs for every input of an ID.

By inputting the ID with whichever method, the assay target animal type is designated preceding the assay. Automatic input by reading automatically from barcodes pasted onto the sample containers or from IC chips would be possible ID input methods. Specifically, animal types as IDs based on 1- or 2-digit numerals or characters are included into specimen numbers for the samples, from which the IDs, in a predetermined position in the specimen number, are read. It should be understood that the IDs can be received via a network from a host computer managing the flow of specimens in the automated analyzing system overall.

Figure 7:
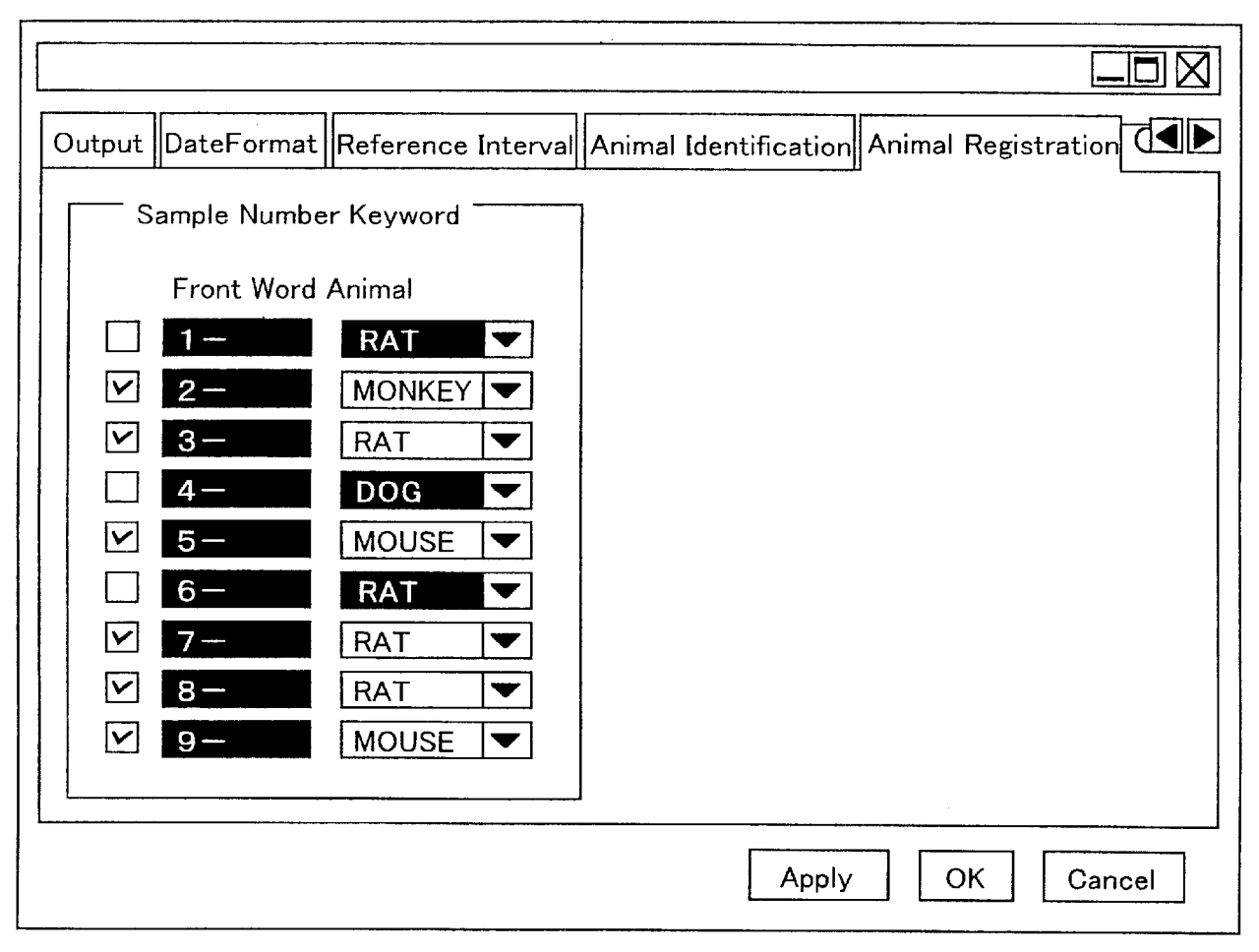

Assigning correspondences in the automated analyzing system between animal types and IDs is preferably user-configurable, as shown in FIG. 7. The user can set the animal type corresponding to each ID to suit his or her own running of the automated analyzing system. In this example, the numeral before the first hyphen in the specimen number is made the ID designating animal type. In the figure, animal type settings have been made by checking checkboxes beside "2," "3," "5," "7," "8" and "9." For example, 2-( . . . ) has been set to designate "monkey," and 3-( . . . ), "rat."

Settings for measurement sensitivity and assaying method are altered according to the animal type inputted as described earlier.

The erythrocyte analyzing unit will now be explained. In humans the average size of red blood cells (mean corpuscular volume, MCV) is 80–90 fl (femtoliters). On the other hand, the average size of platelets (MPV) is considerably smaller, around 10 fl. If one looks at the counts, erythrocytes are several hundred thousand/$\mu$l, which is one figure greater than the 10–30 thousand platelets/$\mu$l. This is smaller than the average red corpuscle size (MCV) for each of the animals—which, for example, is around 70 fl for dogs and rabbits, and around 50 fl for rats and mice. Results from the platelet assay are susceptible to the effects of noise exerted by red blood corpuscles because the erythrocyte analyzing unit assays red blood corpuscles and platelets simultaneously. Therefore, when both are incorporated into the assaying range, the signal detection sensitivity must be set according to the animal type, to enable distinguishing between platelets and the small red blood corpuscles or noise.

Herein, in the present automated analyzing system, the erythrocyte analyzing unit measurement sensitivity corresponding to animal type such as rat or mouse is altered automatically. Specifically, the signal resolution is adapted to the size distribution of the cells that are the target of the assay. Using FIG. 8, switching the gain will be explained as an example of a way to adjust resolution.

Figure 8:
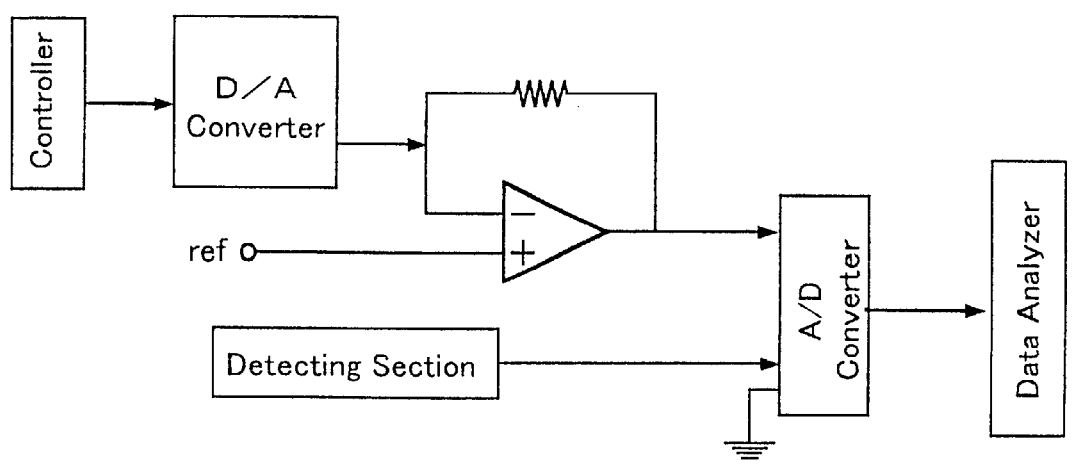
FIG. 8 is an example of a circuit diagram for a signal processor that processes detection signals.

FIG. 8 is an example of a circuit diagram for a signal-processing unit that processes obtained detection signals. The analyzing system switches the base current in response to the animal type that the D/A converter has identified. The detection signal resolution is thereby adapted to the animal type in the A/D converter. Putting the base current to half, for example, halves the largest value of signal by which the process is done, but raises the resolution again as much. This as a result makes it possible to detect tiny cells such as platelets with precision. Accordingly, the detection sensitivity of the erythrocyte detection unit is automatically adapted to an identified animal type.

Next, an explanation of the leukocyte analyzing unit will be made. Leukocytes are 30 fl–250 fl in size and take up broad distribution width. Nonetheless, leukocytes do not include tiny cells such as platelets and therefore in the leukocyte analyzing unit of the present analyzing system the assaying sensitivity does not have to be varied according to animal type.

Figure 9:
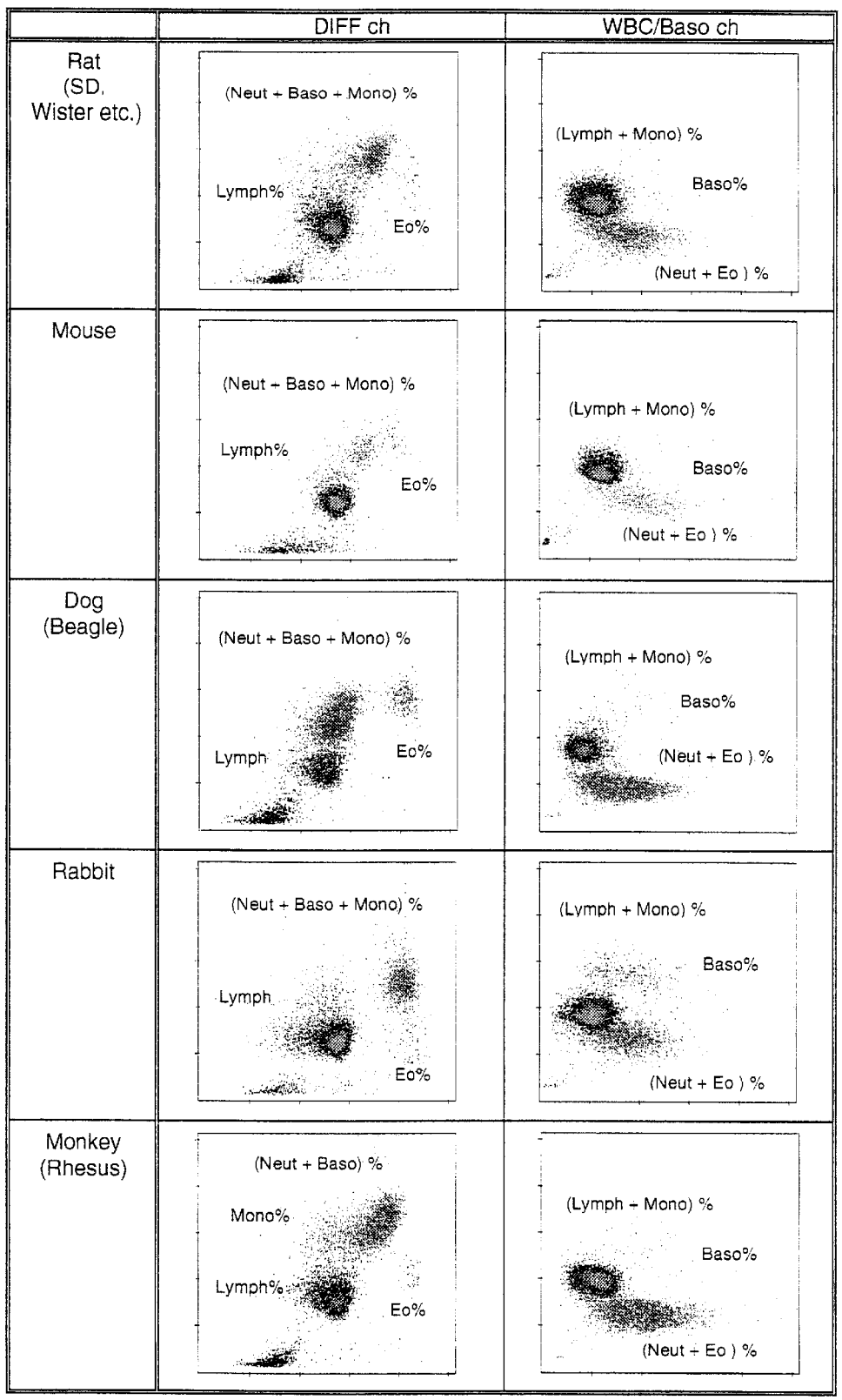
FIG. 9 is scattergrams showing leukocyte assay results for the animal types.

To obtain analytical results for DIFF and WBC/BASO, however, a plurality of populations has to be demarcation-analyzed in a two-dimensional scattergram. FIG. 9 is an example of normal rat, mouse, dog (beagle), rabbit and monkey scattergrams for DIFF and WBC/BASO. As FIG. 9 indicates, percentages, and the size of, and internal information on granules for, the cells in the leukocyte subpopulations differ depending on the animal type. Among the leukocyte subpopulations for instance in the FIG. 9 DIFF scattergrams, for each animal type compare the neutrophil+ basophil population (colored light blue in the figure) position against the large-numbered lymphocyte population (colored pink in the figure). In the monkey it is exhibited diagonally above, exhibited immediately above in the dog (beagle); and in the mouse, it is in a position intermediary between these. Then in humans, it is exhibited in a laterally separated positions, near the position where eosinophils are exhibited. Looking at the percentages, furthermore, the number in the neutrophil+basophil population in the mouse is considerably small compared to the other animal types.

This difference derives from the fact that the size ratios for and inner morphology of each of the cells, in particular the ratio of granules, differs depending on the animal. Note that because rabbit neutrophils possess staining properties resembling eosinophils, there are what is known as false eosinophils.

An analyzing system for human beings has what becomes a reference scattergram by analyzing various human scattergrams beforehand. Then, though assayed populations are exhibited in positions somewhat different from usual, due to such factors in humans as individual differences, disease cases and blood preservation condition, conforming to the reference scattergram, to those positions enables demarcation-analysis. Accordingly conforming to the different animal types fully, however, lowers the precision of the demarcation analysis, and leads to specimens for abnormal disease cases being assayed like normal.

Herein, reference scattergrams in which scattergrams for each animal type are assayed, and reference scattergram conformance parameters are prepared in the present analyzing system. Then utilizing a scattergram analyzing method that corresponds to the animal type selected as the target assay, the assayed scattergram is analyzed.

Furthermore, in assaying cells wherein the number is tiny according to the animal type, increasing the measuring time in the analyzing unit will raise the analyzing precision.

The animal types shown in FIG. 9 can be assayed under the same reagent conditions as for humans, but depending on the animal type, conditions for hemolytic dilution of the samples may have to be varied. It is possible in those cases that the kinds of reagents, and the detection unit, will be altered according to the animal type.

In the present embodiment example, explanation has been made by giving instances that vary any of measurement sensitivity, assay program and reagent conditions. But depending on animal type, it is possible that an automated analyzing system in connection with the present invention analyze by varying all or any arbitrary grouping of these.

Further, the automated analyzing system can output the assay results to a file that includes all of the animal types, or can output them to separate files for each animal type.

Other Embodiment Examples (A) Recording media on which a program that executes the above-described processes of the present invention is recorded are included in the present invention. Computer-readable floppy disks, hard disks, semiconductor memory, CD-ROMs, magneto optical disks (MOs) illustrate examples of recording media.

(B) Transmission media that transmit a program that executes the above-described processes of the present invention are included in the present invention. "Transmission media" include communications media in computer network systems for supplying program information by propagation as carrier waves. Examples that might be given computer networks are LANs, the Internet, and radio communications networks. optical fibers and radio circuitry illustrate examples of communications media.

Utilizing the present invention, input of animal types can be performed readily, which wherein the animal type is to be changed when assaying, alleviates the burdensomeness of the analyzing operation.

That is, because the settings for the analyzing conditions that correspond to the animal type can be set automatically by software just by setting the animal type likewise as the setting for the specimen number, the analyzing operation for a plurality of kinds of animals is readily done.

Various details of the present invention may be changed without departing from its spirit nor its scope. Furthermore, the foregoing description of the embodiments according to the present invention is provided for illustration only, and not for the purpose of limiting the invention as defined by the appended claims and their equivalents.

What is claimed is:

1. An automated analyzing system for analyzing vital samples from different animal types, said automated analyzing system comprising:

an animal type table wherein correspondences between animal types and animal type identifying information are assigned and stored;

identifying information input means for receiving an input of animal type identifying information for each of the vital samples and determining an animal type that corresponds to the animal type identifying information based on said animal type table;

analyzing means for analyzing the vital sample and producing measurement data for the vital sample; and analysis configuration means for altering analysis condition settings of said analyzing means in accordance with said animal type that corresponds to the animal type identifying information received by said identifying information input means.

2. The automated analyzing system set forth in claim 1, wherein said analyzing means includes measuring means that measures the vital sample with electrical signal changes, and said analysis configuration means alters signal resolution of said electrical signal in conformance with the animal type that corresponds to the animal type identifying information.

3. The automated analyzing system set forth in claim 1, wherein said analysis configuration means includes reference measurement data for each of said animal types; and said analysis configuration means assays the measurement data of the vital sample by comparing the measurement data with said reference measurement data of the same animal type.

4. The automated analyzing system set forth in claim 3, wherein said measurement data and reference measurement data are two-or-more-dimensional scattergrams.

5. The automated analyzing system set forth in claim 1, wherein
said identifying information input means automatically reads the animal type identifying information from the vital sample.

6. The automated analyzing system set forth in claim 5, wherein
the animal type identifying information is a part of a barcode, and
said identifying information input means is a barcode reader that reads the barcode attached to the vital sample.

7. The automated analyzing system set forth in claim 1, wherein
said animal type identifying information is one of numerals and characters, and
said identifying information input means receives the input of animal type identifying information by reading specimen identifying information of the vital sample, the animal type identifying information being a part of the specimen identifying information.

8. The automated analyzing system set forth in claim 7, wherein
the specimen identifying information includes a hyphen and a portion preceding the hyphen, the portion preceding the hyphen including one of numerals and characters, and
said identifying information input means receives the input of animal type identifying information by reading the portion preceding the hyphen of the specimen identifying information of the vital sample.

9. The automated analyzing system set forth in claim 1, further comprising
adjusting means for adjusting the correspondences between said animal types and said animal type identifying information in said animal type table.

10. The automated analyzing system set forth in claim 1, wherein
said analysis configuration means alters the analysis condition settings by altering a measurement sensitivity of said analyzing means.

11. The automated analyzing system set forth in claim 1, wherein
said analyzing means has an assay program, and
said analysis configuration means alters the analysis condition settings of said analyzing means by altering said assay program.

12. A computer-readable recording medium for use in an automated analyzing system that analyzes vital samples from different animal types, said recording medium having a program that executes steps of:
preparing an animal table in which correspondences between animal types and animal type identifying information are assigned and stored, the correspondences between the animal types and the animal type identifying information in the animal table being adjustable;
receiving an input of animal type identifying information for each of the vital samples and determining an animal type that corresponds to the animal type identifying information based on the animal type table;
altering analysis condition settings of the analyzing system in accordance with the animal type that corresponds to the animal type identifying information; and
analyzing the vital sample and producing measurement data for the vital sample.

13. A transmission medium for use in an automated analyzing system that analyzes vital samples of different animal types, said transmission medium transmitting a program that executes steps of:
preparing an animal table in which correspondences between animal types and animal type identifying information are assigned and stored, the correspondences between the animal types and the animal type identifying information in the animal table being adjustable;
receiving an input of animal type identifying information for each of the vital samples and determining an animal type that corresponds to the animal type identifying information based on the animal type table;
altering analysis condition settings of the analyzing system in accordance with the animal type that corresponds to the animal type identifying information; and
analyzing the vital sample and producing measurement data for the vital sample.

14. An automated analyzing system for analyzing vital samples from different animal types, said automated analyzing system comprising:
sample containers having animal type identifying information thereon;
an animal type table wherein correspondences between animal type and said animal type identifying information designating said animal type are assigned and stored;
animal type input means for receiving said animal type identifying information from said sample containers and determining an animal type that corresponds to said animal type identifying information based on said animal type table;
analyzing means for analyzing the vital samples in said sample containers and producing measurement data for each vital sample; and
analysis configuration means for altering analysis condition settings of said analyzing means in accordance with said animal type that corresponds to said animal type identifying information received by said animal type input means.

15. The automated analyzing system set forth in claim 14, wherein
said analyzing means includes measuring means that measures the vital samples with electrical signal changes; and
said analysis configuration means alters signal resolution of said electrical signal in conformance with said animal type that corresponds to said animal type identifying information.

16. The automated analyzing system set for the in claim 14, wherein
said analysis configuration means includes reference measurement data that corresponds to each of said animal types;
said analysis configuration means assays said measurement data by comparing said measurement data with said reference measurement data of the same animal type.

17. The automated analyzing system set forth in claim 16, wherein
said measurement data and reference measurement data are two-or-more-dimensional scattergrams.

18. The automated analyzing system set forth in claim 14, further comprising:

adjusting means for adjusting correspondences between said animal types and said animal type identifying information designating said animal type in said animal type table.

19. The automated analyzing system set forth in claim 14, wherein said animal type identifying information is one of numerals and characters, and said identifying information input means receives the input of animal type identifying information by reading specimen identifying information of the vital sample, the animal type identifying information being a part of the specimen identifying information.

20. The automated analyzing system set forth in claim 19, wherein the specimen identifying information includes a hyphen and a portion preceding the hyphen, the portion preceding the hyphen including one of numerals and characters, and said identifying information input means receives the input of animal type identifying information by reading the portion preceding the hyphen of the specimen identifying information of the vital sample.

21. The automated analyzing system set forth in claim 14, wherein said analysis configuration means alters the analysis condition settings by altering a measurement sensitivity of said analyzing means.

22. The automated analyzing system set forth in claim 14, wherein said analyzing means has an assay program, and said analysis configuration means alters the analysis condition settings of said analyzing means by altering said assay program.

* * * * *